(12) United States Patent
Cohen et al.

(10) Patent No.: US 8,551,137 B2
(45) Date of Patent: Oct. 8, 2013

(54) DOUBLE THREADED TISSUE TACK

(75) Inventors: Matthew Cohen, Berlin, CT (US); Michael Primavera, Orange, CT (US)

(73) Assignee: Covidien LP, Mansfield, MA (US)

( * ) Notice: Subject to any disclaimer, the term of this patent is extended or adjusted under 35 U.S.C. 154(b) by 421 days.

(21) Appl. No.: 12/512,377

(22) Filed: Jul. 30, 2009

(65) Prior Publication Data
US 2010/0049244 A1 Feb. 25, 2010

Related U.S. Application Data

(60) Provisional application No. 61/090,288, filed on Aug. 20, 2008.

(51) Int. Cl.
*A61B 17/08* (2006.01)

(52) U.S. Cl.
USPC .......................................................... 606/213

(58) Field of Classification Search
USPC ............. 606/75, 99, 104, 139, 142, 213, 219, 606/232; 81/52, 53.2; 411/388–389
See application file for complete search history.

(56) References Cited

U.S. PATENT DOCUMENTS

| | | | |
|---|---|---|---|
| 71,909 A * | 12/1867 | Pierce | 411/389 |
| 188,668 A * | 3/1877 | Pleukharp | 411/389 |
| 1,644,477 A * | 10/1927 | Klaus | 411/389 |
| 1,897,196 A * | 2/1933 | Hunt | 411/389 |
| 3,276,172 A * | 10/1966 | Alvden | 52/127.12 |
| 4,064,772 A * | 12/1977 | Boyd et al. | 81/57.13 |
| 4,157,674 A * | 6/1979 | Carlson et al. | 411/389 |
| 4,175,555 A | 11/1979 | Herbert | |
| 4,640,271 A | 2/1987 | Lower | |
| 4,723,541 A | 2/1988 | Reese | |
| 4,928,558 A | 5/1990 | Makhlouf | |
| 5,019,079 A | 5/1991 | Ross | |
| 5,035,716 A | 7/1991 | Downey | |
| 5,062,851 A | 11/1991 | Branemark | |
| 5,108,443 A | 4/1992 | Branemark | |
| 5,129,906 A * | 7/1992 | Ross et al. | 606/77 |

(Continued)

FOREIGN PATENT DOCUMENTS

| | | |
|---|---|---|
| DE | 9014141 U1 | 2/1992 |
| DE | 4029087 A1 | 5/1992 |

(Continued)

OTHER PUBLICATIONS

European Search Report for EP 10177651.6-1526 date of completion is Dec. 14, 2010 (3 pages).

(Continued)

*Primary Examiner* — Corrine M McDermott
*Assistant Examiner* — Son Dang

(57) ABSTRACT

There is disclosed a threaded tissue tack for use in approximating and securing a pair of tissue sections together. The threaded tissue tack has a central body portion and first and second screws extending from opposite ends of the central body portion. The first screw includes a left-hand thread and the second includes a right-hand thread. Engagement structure is provided on the central body portion to rotate the threaded tissue tack about its longitudinal axis and into the pair of tissue sections. There is also disclosed a tack driver for rotating the threaded tissue tack into the tissue. Guards are provided intermediate first and second ends of the central body portion and the first and second screws to protect surrounding tissue from the tack driver.

12 Claims, 4 Drawing Sheets

(56) References Cited

U.S. PATENT DOCUMENTS

| | | | |
|---|---|---|---|
| 5,277,087 A * | 1/1994 | Wilson et al. | 81/57.29 |
| 5,307,713 A * | 5/1994 | White | 81/180.1 |
| 5,354,305 A | 10/1994 | Lewis, Jr. et al. | |
| 5,409,486 A | 4/1995 | Reese | |
| 5,417,692 A * | 5/1995 | Goble et al. | 606/311 |
| 5,507,211 A | 4/1996 | Wagner | |
| 5,536,127 A | 7/1996 | Pennig | |
| 5,540,122 A | 7/1996 | Lund | |
| H1689 H * | 11/1997 | Foucher | 81/124.3 |
| 5,769,583 A * | 6/1998 | Girbinger | 411/389 |
| 5,827,285 A | 10/1998 | Bramlet | |
| 5,879,396 A | 3/1999 | Walston et al. | |
| 5,954,723 A | 9/1999 | Spetzler | |
| 6,039,738 A | 3/2000 | Sanders et al. | |
| 6,261,292 B1 | 7/2001 | Diebold et al. | |
| 6,306,140 B1 | 10/2001 | Siddiqui | |
| 6,458,134 B1 * | 10/2002 | Songer et al. | 606/304 |
| 6,475,242 B1 | 11/2002 | Bramlet | |
| 6,743,233 B1 | 6/2004 | Baldwin et al. | |
| 7,044,031 B1 * | 5/2006 | Mullen | 81/121.1 |
| 7,044,953 B2 | 5/2006 | Capanni | |
| 7,255,523 B2 | 8/2007 | Laan | |
| 2002/0077661 A1 | 6/2002 | Saadat | |
| 2003/0032961 A1 | 2/2003 | Pelo et al. | |
| 2004/0010275 A1 | 1/2004 | Jacobs et al. | |
| 2004/0060409 A1 | 4/2004 | Leung et al. | |
| 2005/0177165 A1 | 8/2005 | Zang et al. | |
| 2006/0052878 A1 | 3/2006 | Schmieding | |
| 2006/0241621 A1 | 10/2006 | Moskowitz et al. | |
| 2007/0059114 A1 * | 3/2007 | Grimes, II | 408/238 |

FOREIGN PATENT DOCUMENTS

| | | |
|---|---|---|
| DE | 19840916 A1 | 3/2000 |
| EP | 0499038 A2 | 8/1992 |
| FR | 2863154 A1 | 6/2005 |
| GB | 2239415 A | 7/1991 |
| WO | WO97/05830 A1 | 2/1997 |

OTHER PUBLICATIONS

European Search Report for EP 09251998.2-2310 date of completion is Apr. 21, 2010 (5 pages).

* cited by examiner

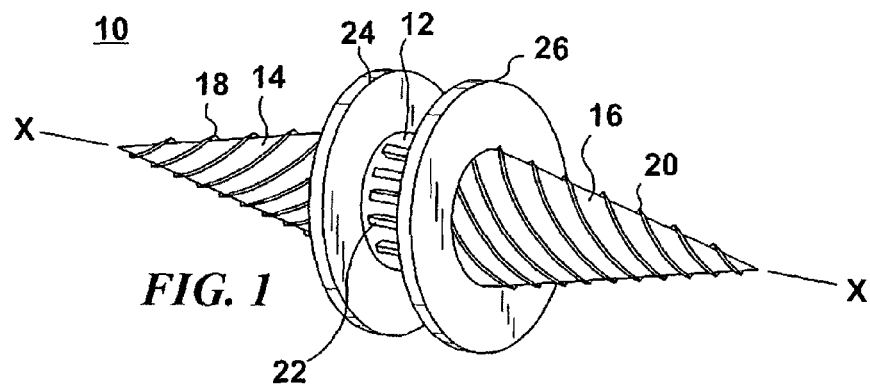
FIG. 1
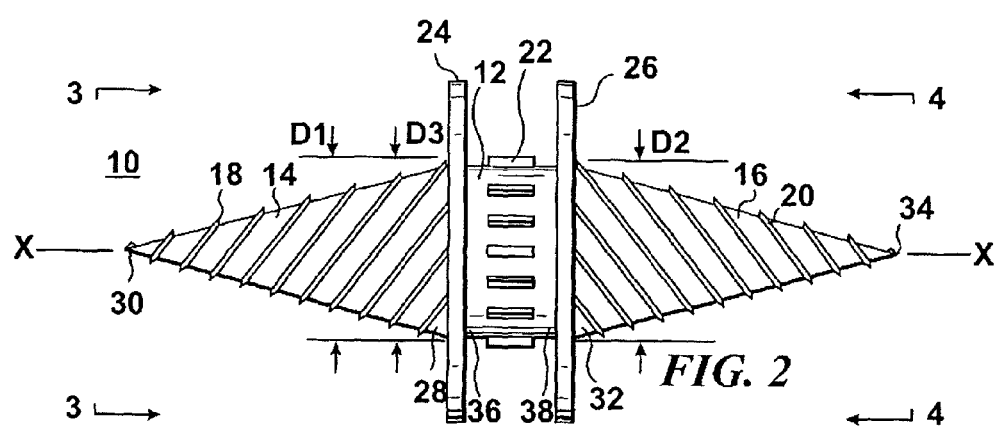
FIG. 2
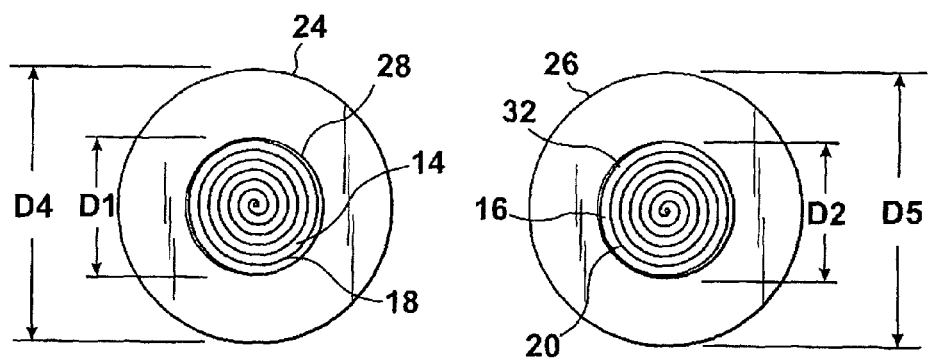
FIG. 3
FIG. 4

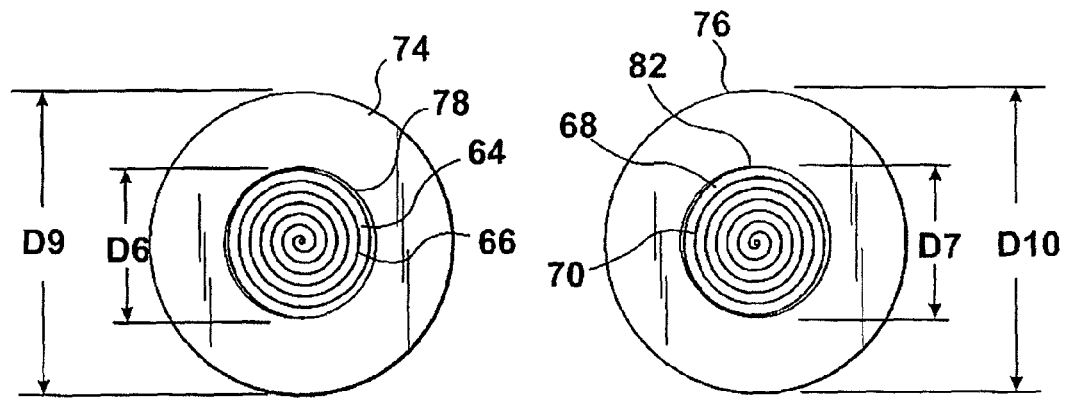
FIG. 8  FIG. 9
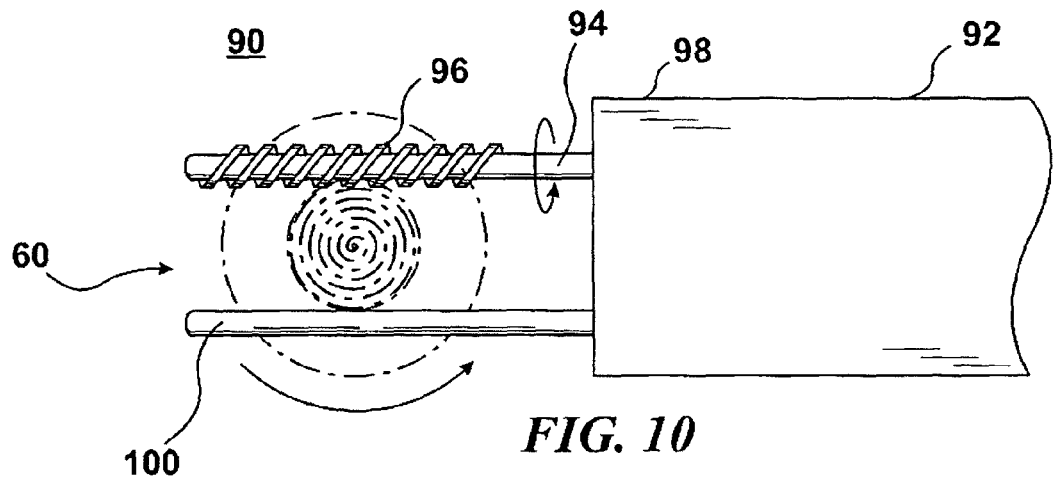
FIG. 10

DOUBLE THREADED TISSUE TACK

CROSS-REFERENCE TO RELATED APPLICATION

The present application claims the benefit of and priority to U.S. Provisional Application Ser. No. 61/090,288, filed on Aug. 20, 2008, the entire disclosure of which is incorporated herein by reference.

BACKGROUND

1. Technical field

The present disclosure relates to a threaded tissue tack for use in surgical procedures to join tissue sections. More particularly, the present disclosure relates to a tissue tack having right and left hand threaded ends for rotation into a pair of tissue sections to approximate and secure the tissue sections together.

2. Background of Related Art

Various surgical procedures require joining tissue sections. This is typically accomplished by approximating or moving a pair of tissue sections adjacent each other with a pair of tissue clamps and subsequently stapling or suturing the tissue sections together. The tissue sections need to be held together with the clamps during the suturing or stapling processes. This requires a certain amount of space within the operative site as well as the need to manipulate multiple surgical instruments.

Therefore, a need exists for an implantable surgical device which is capable of both approximating a pair of tissue sections together and securing the tissue sections to each other. A further need exists for a threaded tissue tack to draw the tissue sections together and hold them together while healing.

SUMMARY

There is disclosed a threaded tissue tack including a central body portion having a first end and a second end. A first screw extends from the first end of the central body portion and a second screw extends from the second end of the central body portion. The first screw includes a left-hand thread formed thereon and the second screw includes a right-hand thread formed thereon. The first screw includes a conical member having a base and a tissue penetrating tip. A diameter of the base is substantially identical to a diameter of the central body portion. The second screw also includes a conical member having a base and a tissue penetrating tip. The central body portion includes engagement structure for engagement with a tack driver.

In one embodiment, the engagement structure is a plurality of teeth formed about a circumference of the central body portion. In an alternative embodiment, the engagement structure is a plurality of slots formed in a circumference of the central body portion.

In a specific embodiment, a first guard is located between the first screw and the central body portion and a second guard is located between the second screw and the central body portion. The first and second guards are generally disk shaped and have diameters substantially greater than a diameter of the central body portion.

In one embodiment, the threaded tissue tack is formed of a biocompatible material. In a specific embodiment, the threaded tissue tack is formed of a bioabsorbable material.

There is also disclosed a system for approximating and securing a pair of tissue sections together. The system includes a tissue tack and a tack driver. The tissue tack includes a central body portion and a first and second screws extending from opposite ends of the central body portion. The central body portion includes driven structure. The tack driver is provided for rotating the tissue tack. The tack driver includes a housing having a power source and drive structure extending from the housing and movable by the power source. The drive structure of the tack driver is engageable with the driven structure of the tissue tack to rotate the tissue tack about its longitudinal axis.

In one embodiment, the driven structure is a plurality of teeth formed about a circumference of the central body portion and the drive structure includes a movable drivetrain, having a plurality of teeth, extending distally from the housing such that the plurality of teeth are engageable with the plurality of teeth formed on the central body portion to rotate the tissue tack.

In an alternative embodiment, the driven structure is a plurality of slots formed in a circumference of the central body portion and the drive structure includes a rotatable drive shaft having a helical thread formed thereon. The helical thread is engageable with the plurality of slots formed in the circumference of the central body portion to rotate the tissue tack.

In a specific embodiment, the tack driver includes a support bar extending distally from the housing such that the tissue tack rests on the support bar.

There is further disclosed a method of securing a pair of tissue sections together. A tissue tack is provided having a central body portion and first and second screws extending from the central body portion. The first screw has a left-hand thread and the second screw has a right-hand thread. The tissue tack is positioned between a first tissue section and a second tissue section. The first and second tissue sections are engaged with tissue penetrating tips of the first and second screws and the tissue tack is rotated about a longitudinal axis of the tissue tack to drive the first and second screws into the first and second tissue sections.

DESCRIPTION OF THE DRAWINGS

Various embodiments of the presently disclosed double threaded tissue tack disclosed herein with reference to the drawings, wherein:

FIG. 1 is a perspective view of one embodiment of a double threaded tissue tack;

FIG. 2 is a side view of the double threaded tissue tack of FIG. 1;

FIG. 3 is an end view of the double threaded tissue tack of FIG. 2;

FIG. 4 is an opposite end view of the double threaded tissue tack of FIG. 2;

FIG. 8 is an end view of the double threaded tissue tack of FIG. 7;

FIG. 9 is an opposite end view of the double threaded tissue tack of FIG. 7;

FIG. 10 is a side view of an alternative embodiment of a tack driver for use with the double threaded tissue tack of FIG. 6;

DETAILED DESCRIPTION OF EMBODIMENTS

Figure 5:
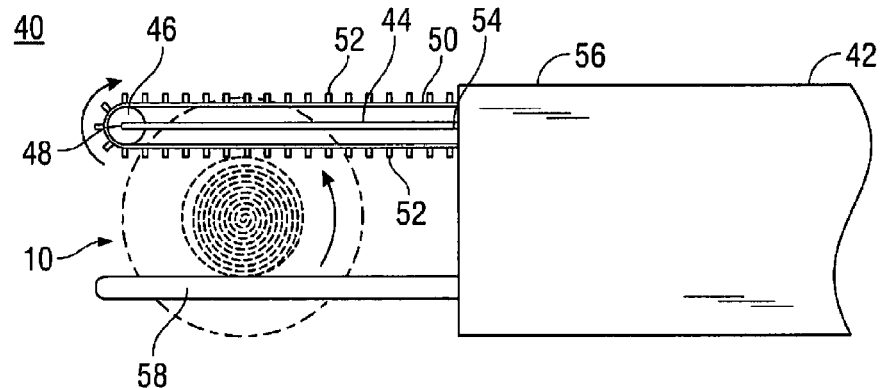
FIG. 5 is a side view of one embodiment of a tack driver for use with the double threaded tissue tack of FIG. 1.

Embodiments of the presently disclosed threaded tissue tack will now be described in detail with reference to the drawings wherein like numerals designate identical or corresponding elements in each of the several views. As is common in the art, the term "proximal" refers to that part or component closer to the user or operator, i.e., surgeon or physician, while the term "distal" refers to that part or component further away from the user.

Referring to FIGS. 1 and 2, there is disclosed a first embodiment of a double threaded tissue tack 10 for use in approximating and securing a pair of tissue sections together. Tissue tack 10 generally includes a cylindrical, central body portion 12 and first and second conical members 14 and 16, respectively, extending from central body portion 12. In order to rotate tissue tack 10 into a pair of tissue sections simultaneously, first conical number 14 is provided with a left-hand thread 18 and second conical number 16 is provided with a right-hand thread 20. In a specific embodiment, left-hand thread 18 and right-hand thread 20 have identical pitches. A plurality of tabs or teeth 22 are provided about the circumference of central body portion 12 to facilitate rotating tissue tack 10 into tissue in a manner described hereinbelow. Thus, as tissue tack 10 is rotated about a longitudinal axis x-x of tissue tack 10, left-hand thread 18 and right-hand thread 20 are simultaneously rotated into the tissue sections.

Tissue tack 10 may additionally includes a first guard 24 interposed between cylindrical body portion 12 and first conical member 14 and a second guard 26 interposed between second conical member 16 and cylindrical body portion 12. First and second guards 24 and 26, respectively, are provided to shield surrounding tissue sections against a driver used to rotate threaded tissue tack 10 into the tissue in a manner described in more detail hereinbelow.

Tissue tack 10 may be formed from a variety of materials. For example, tissue tack 10 may be formed from biocompatible materials such as, for example, stainless steel, titanium, plastics, ceramics, etc. In a specific embodiment, tissue tack 10 is formed from a bioabsorbable or resorbable material such that tissue tack 10 degrades over time as the secured tissue structures heal together. Additionally, tissue tack 10 may incorporate various other materials, such as, for example, medicants, sealant materials, bioactive agents and the like.

With reference to FIG. 2, left-hand thread 18 extends from a base 28 of first conical member 14 to a tissue penetrating tip 30 of first conical member 14. Similarly, right-hand thread 20 extends from a base 32 of the second conical member 16 to a tissue penetrating tip 34 of second conical member 16. As shown, first conical member 14 extends from a first end 36 a central body portion 12 and second conical member 16 extends from the second end 38 of central body portion 12. It should be noted that first and second guards 24 and 26 may be integrally formed with central body portion 12 or may be provided as auxiliary structures affixed to respective first and second ends 36 and 38 of central body portion 12.

In this embodiment, diameters D1 and D2 of bases 28 and 32 of first and second conical members 14 and 16 are substantially identical to a diameter D3 of central body portion 12. This facilitates forming tissue tack 10 from a single, cylindrical length of material. Alternatively, diameters D1 and D2 of bases 28 and 32 may differ from diameter D3 of central body portion 12 to change the profiles of the "screws" provided by first conical member 14 and left-hand thread 18 and second conical member 16 and right-hand thread 20. For example, an elongate and smaller diameter profile for the "screws" may be desirable where tissue tack 10 is to be used in relatively hard or narrow diameter tissues such as bone, while a shorter and larger diameter profile for the "screws" may be desirable where tissue tack 10 is utilized in relatively large, soft tissue sections.

Referring for the moment to FIGS. 3 and 4, it can be seen that a diameter D4 of first guard 24 is greater than diameter D3 of central body portion 12 (FIG. 3). Similarly, a diameter D5 of second guard 26 is greater than diameter D3 of central body portion 12 (FIG. 4). The degree of difference in diameters D4 and D5, of first and second guards 24 and 26 respectively, from diameter D3 of central body portion 12 is tailored to accommodate the types of tissue being connected. For example, where relatively small diameter tissues are being connected, diameters D4 and D5 can be chosen to be similar to diameter D3. Additionally, diameters D4 and D5 may be chosen to be significantly greater than diameter D3 when necessary to shield surrounding tissues from a driver used with tissue tack 10 in a manner described in more detail below.

Referring now to FIG. 5, there is disclosed one embodiment of a tack driver 40 for use in rotating tissue tack 10 into tissue. Driver 40 generally includes a motor housing 42 containing a power source or drive motor (not shown) and a guide bar 44 extending distally from motor housing 42. A guide wheel 46 is provided on a distal end 48 of guide bar 44. A drive chain 50, having a plurality of chain teeth 52 thereon, extends from motor housing 42 and around guide wheel 46 and guide bar 44 and is driven by the power source. As shown, a proximal end 54 of guide bar 44 extends from a distal end 56 of motor housing 42. Motor housing 42, including the power source, is provided to rotate drive chain 50, including chain teeth 52, about guide bar 44 and guide wheel 46. As drive chain 50 rotates, chain teeth 52 engage teeth 22 on central body portion 12 of threaded tissue tack 10 to rotate threaded tissue tack 10 into tissue.

A support bar 58 extends from distal end 56 of motor housing 42 and is provided to support tissue tack 10 during engagement with drive chain 50 of driver 40. Upon engagement of tissue tack 10 with tack driver 40, support bar 58 of tack driver 40 may be located underneath teeth 22 on central body portion 12 of tissue tack 10 or, alternatively, may be located alongside teeth 22 of tissue tack 10 and vertically offset from guide bar 44 of tack driver 40.

Figure 6:
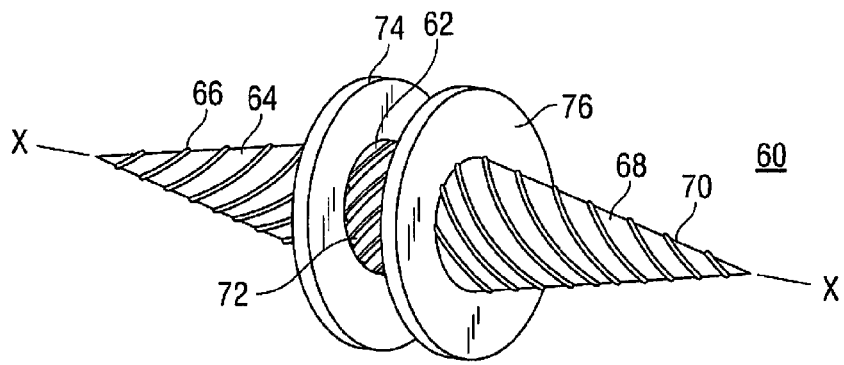
FIG. 6 is a perspective view of an alternative embodiment of a double threaded tissue tack.
Figure 7:
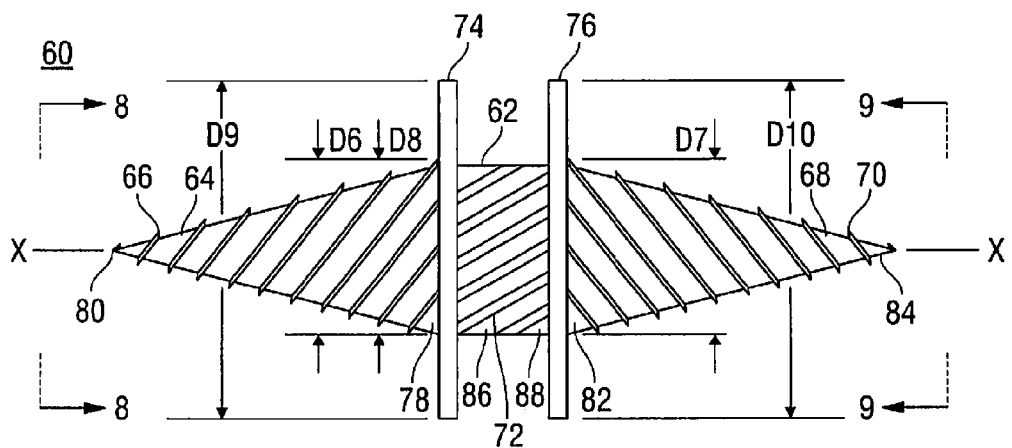
FIG. 7 is a side view of the double threaded tissue tack of FIG. 6.

Referring now to FIGS. 6 and 7, there is disclosed an alternative embodiment of a threaded tissue tack 60 for use in securing a pair of tissue sections together. Similar to tissue tack 10 described herein above, tissue tack 60 generally includes a cylindrical central body portion 62 and a pair of "screws" formed from a first conical member 64 having a left-hand thread 66 and a second conical member 68 having a right-hand thread 70, both extending from central body portion 62. In contrast to threaded tissue tack 10 described herein above, central body portion 62 of threaded tissue tack 60 is provided with a plurality of slots 72 formed in the circumference of central body portion 62. Slots 72 are provided to be engaged by a tack driver as described in more detail hereinbelow in order to rotate threaded tissue tack 60 about its longitudinal axis x-x and into tissue. First and second guards 74 and 76, respectively, are provided on threaded tissue tack 60 and function in substantially the same manner with regard to first and second guards 24 and 26 included in tissue tack 10.

Threaded tissue tack 60 may be formed from various biocompatible or bioabsorbable materials similar to those described herein above.

With specific reference to FIG. 7, first cylindrical member 64 includes a base 78 and a tissue penetrating tip 80. Left-hand thread 66 extends from base 78 to tissue penetrating tip 80. Similarly, second conical member 68 includes a base 82 and a tissue penetrating tip 84. Right-hand thread 70 extends from base 82 to tissue penetrating tip 84. First conical member 64 extends from a first end 86 of central body portion 62 while second conical member 68 extends from a second end 88 of central body portion 62. As shown, diameters D6 and D7 of bases 78 and 82 of first and second conical members 64 and 68 respectively, are substantially identical to a diameter D8 of central body portion 62. As was disclosed with respect to tissue tack 10 described herein above, these diameters may vary from each other depending upon the nature of the tissue operated upon and the tack driver used to rotate threaded tissue tack 60.

Referring for the moment to FIGS. 7, 8 and 9, a diameter D9 of first guard 74 is substantially greater than diameter D6 of the base 78 of first conical member 64 (FIGS. 7 and 8). Likewise, a diameter D10 of second guard 76 is substantially greater than diameter D7 of base 82 of second conical member 68 (FIGS. 7 and 9). Again, these relative diameters may vary depending upon the nature of the tissue and the tack driver being used.

Referring now to FIG. 10, there is disclosed an alternative embodiment of a tack driver 90 particularly suited for use with threaded tissue tack 60. Tack driver 90 generally includes a motor housing 92 including a drive motor (not shown) and a rotating driveshaft 94 extending distally from motor housing 92. Driveshaft 94 is provided with a helical drive screw 96 formed thereon to engage slots 72 formed in central body portion 62 of threaded tissue tack 60. Driveshaft 94 extends from a distal end 98 of motor housing 92. Similar to tack driver 40 described herein above, tack driver 90 includes a support bar 100 extending distally from distal end 98 of motor housing 92.

Upon engagement of tack driver 98 with threaded tissue tack 60, helical drive screw 96 engages slots 72 and threaded tissue tack 60. As driveshaft 94 is rotated, threaded tissue tack 60 is rotated about its longitudinal axis. Support bar 100 may be positioned in a vertical alignment with rotating driveshaft 94 or, alternatively, maybe vertically offset from rotating driveshaft 94 to avoid damage to slots 72 in central body portion 62 of threaded tissue tack 60 as threaded tissue tack 68 is rotated by tack driver 90.

Figure 11:
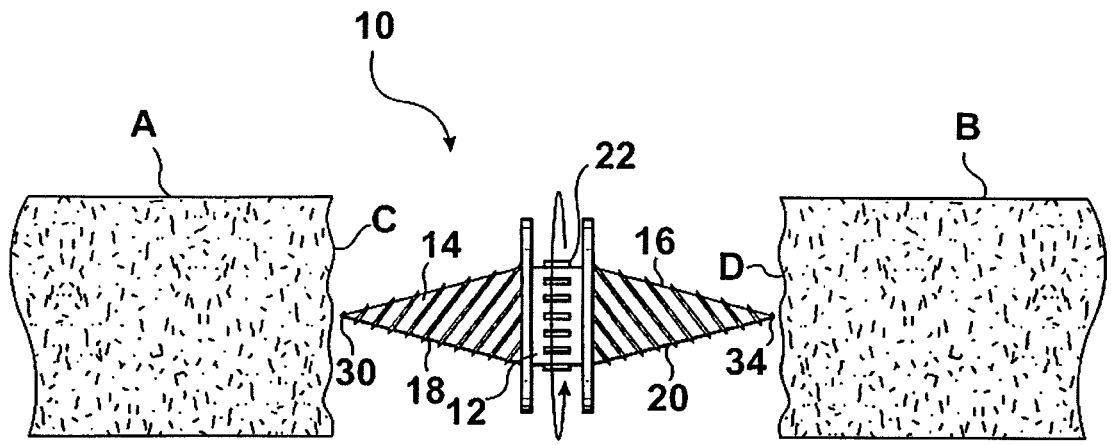
FIG. 11 is a side view of the double threaded tissue tack of FIG. 1 positioned between a pair of tissue sections.
Figure 12:
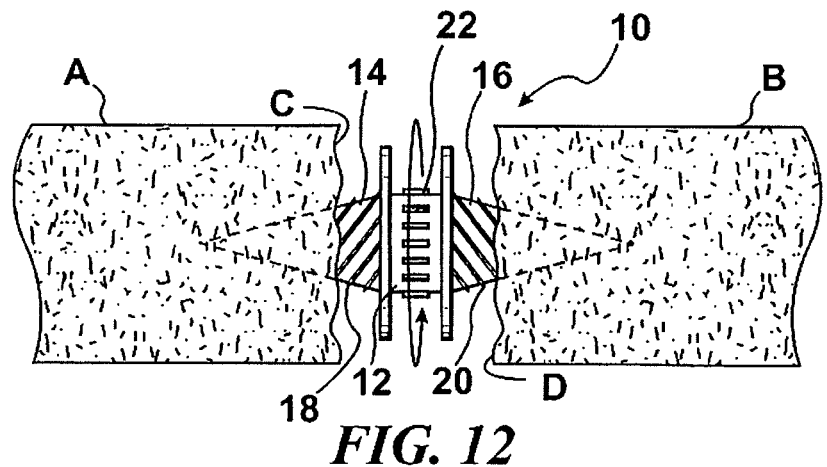
FIG. 12 is a side view, similar to FIG. 11, illustrating the double threaded tissue tack partially rotated into the pair of tissue sections.
Figure 13:
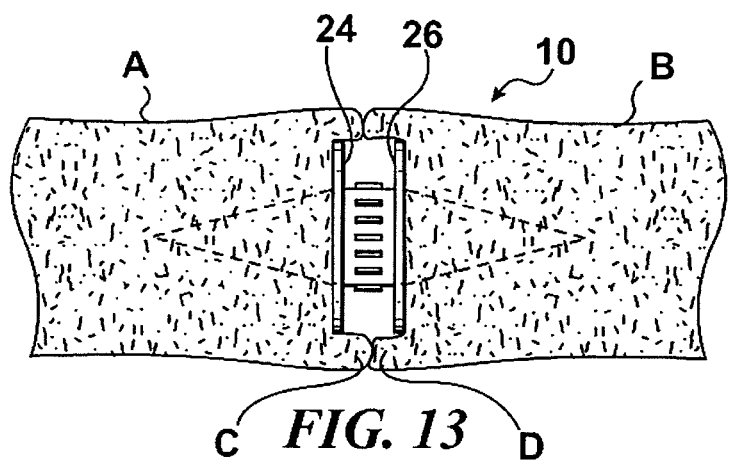
FIG. 13 is a side view, similar to FIG. 12, with the double threaded tissue tack fully rotated into the pair of tissue sections.

Referring now to FIGS. 11, 12 and 13, the use of threaded tissue tack 10 to approximate and secure a pair of tissue sections A and B together will now be described. While the following description is given with regard to tissue tack 10, it should be appreciated that a similar procedure is applicable for use of alternative embodiments, such as tissue tack 60. Referring initially to FIG. 11, threaded tissue tack 10 is positioned between tissue sections A and B such that the screws formed by first conical portion 14 and left-hand thread 18 and second conical portion 16 and right-hand thread 20 are adjacent opposing free ends C and D of tissue sections A and B. Specifically, tissue penetrating tip 30 of first conical portion 14 is positioned adjacent free end C of tissue section A while tissue penetrating tip 34 of second conical portion 16 is positioned adjacent free end D of tissue section B.

Once threaded tissue tack 10 has been properly positioned between tissue sections A and B, tissue tack 10 may be engaged by a tack driver such as, for example, tack driver 40 described herein above. Specifically, teeth 22 formed on central body portion 12 of threaded tissue tack 10 are engaged by the tack driver and the tack driver it is actuated to rotate threaded tissue tack 10 about its longitudinal axis.

Referring to FIG. 12, as tissue tack 10 is rotated, tissue penetrating tips 30 and 34 penetrate into and engage opposed facing surfaces C and D of tissue sections A and B. Thereafter, left-hand thread 18 formed in first conical portion 14 and right-hand thread 20 formed in second conical portion 16 engage opposed facing surfaces C and D of tissue sections A and B thus drawing first conical portion 14 into tissue section A and drawing second conical portion 16 into tissue section B to approximate the tissues. As noted herein above, the opposite rotational orientation of left-hand thread 18 and right-hand thread 20 enable threaded tissue tack 10 to be rotated in a single direction while driving of the "screws" simultaneously into the adjacent tissue sections.

Referring to FIG. 13, threaded tissue tack 10 continues to be rotated drawing tissue sections A and B together until facing surfaces C and D of tissue sections A and B are drawn together to abut each other. First and second guards 24 and 26 shield tissue sections A and B and prevent damage to tissue sections A and B from engagement with the tack driver. Thereafter, the tack driver can be removed from engagement with tissue tack 10 leaving tissue tack 10 in place within the tissues and allowing the tissues to heal. As noted herein above, tissue tack 10 maybe formed of a permanent, biocompatible material, bioabsorbable material or combinations thereof. Additionally, tissue tack 10 may incorporate various medicants and tissue sealants to facilitate and promote healing of the connective tissues. Thus, tissue tack 10 forms a unique and novel device for approximating a pair of tissue sections and connecting the tissue sections together.

It will be understood that various modifications may be made to the embodiments and methods of use disclosed herein. For example, either of the disclosed tack drivers may be used with either of the disclosed threaded tissue tacks or other manual or powered devices configured to rotate the threaded tissue tacks may be incorporated. Further, alternative structure such as, for example, angled ribs, helical threads, etc. may be provided on the central body portions of the disclosed tissue tacks to facilitate rotating the disclosed tissue tacks into tissue. Additionally, the disclosed threads need not extend along the entire lengths of the associated conical sections of may be incorporated only along particular lengths thereof. Therefore, the above description should not be construed as limiting, but merely as exemplifications of particular embodiments. Those skilled in the art will envision other modifications within the scope and spirit of the claims appended hereto.

The invention claimed is:

1. A system for approximating and securing a pair of tissue sections together comprising:
   a tissue tack including a central body portion and a first screw and a second screw extending from opposite ends of the central body portion, the central body portion including a driven structure;
   a first guard located between the first screw and the central body portion and a second guard located between the second screw and the central body portion, wherein diameters of the first and second guards are substantially greater than a diameter of the central body portion; and
   a tack driver for rotating the tissue tack into a pair of tissue sections simultaneously, the tack driver including a housing having a power source and drive structure extending from the housing and movable by the power source, wherein the drive structure of the tack driver is engageable with the driven structure of the tissue tack to rotate the tissue tack about its longitudinal axis.

2. The system as recited in claim 1, wherein the drive structure includes a rotatable drive shaft having a helical thread formed thereon such that the helical thread is engageable with a plurality of slots formed in the circumference of the central body portion to rotate the tissue tack.

3. The system as recited in claim 1, further comprising a support bar extending distally from the housing such that the tissue tack rests on the support bar.

4. The system as recited in claim 1, wherein the first screw includes a conical member having a base and a tissue penetrating tip.

5. The system as recited in claim 4, wherein a diameter of the base is substantially identical to a diameter of the central body portion.

6. The system as recited in claim 1, wherein the second screw includes a conical member having a base and a tissue penetrating tip.

7. The system as recited in claim 1, wherein the first and second guards are disk shaped.

8. The system as recited in claim 1, wherein the first and second screws and the central body portion are formed of a biocompatible material.

9. The system as recited in claim 1, wherein the first and second screws and the central body portion are formed of a bioabsorbable material.

10. A system for approximating and securing a pair of tissue sections together comprising:
   a tissue tack including a central body portion and a first screw and a second screw extending from opposite ends of the central body portion, the central body portion including a driven structure; and
   a tack driver for rotating the tissue tack into a pair of tissue sections simultaneously, the tack driver including a housing having a power source and drive structure extending from the housing and movable by the power source, wherein the drive structure of the tack driver is engageable with the driven structure of the tissue tack to centrally drive the tissue tack about its longitudinal axis and includes a rotatable drive shaft having a helical thread formed thereon such that the helical thread is engageable with a plurality of slots formed in the circumference of the central body portion to rotate the tissue tack.

11. The system as recited in claim 10, further comprising a first guard located between the first screw and the central body portion and a second guard located between the second screw and the central body portion.

12. The system as recited in claim 11, wherein diameters of the first and second guards are substantially greater than a diameter of the central body portion.

\* \* \* \* \*